(12) United States Patent
Xu et al.

(10) Patent No.: US 8,715,681 B2
(45) Date of Patent: May 6, 2014

(54) MINIMAL MOTIFS OF LINEAR B-CELL EPITOPES IN L1 PROTEIN FROM HUMAN PAPILLOMAVIRUS TYPE 58 AND THEIR APPLICATIONS

(75) Inventors: Wanxiang Xu, Shanghai (CN); Shaohua Gu, Shanghai (CN); Yaping He, Shanghai (CN); Chaoneng Ji, Shanghai (CN); Haiping Tang, Shanghai (CN); Jian Wang, Shanghai (CN); Zhida Sun, Shanghai (CN); Yi Xie, Shanghai (CN)

(73) Assignee: Hengsun Pharmaceutical Technology Co. Ltd., Guangzhou (CN)

( * ) Notice: Subject to any disclaimer, the term of this patent is extended or adjusted under 35 U.S.C. 154(b) by 0 days.

(21) Appl. No.: 13/364,952

(22) Filed: Feb. 2, 2012

(65) Prior Publication Data

US 2013/0202632 A1    Aug. 8, 2013

(51) Int. Cl.
*A61K 39/00* (2006.01)
*C07K 5/00* (2006.01)

(52) U.S. Cl.
USPC ............ 424/185.1; 530/300; 424/204.1

(58) Field of Classification Search
None
See application file for complete search history.

(56) References Cited

U.S. PATENT DOCUMENTS 7,026,443 B1 *   4/2006   Sette et al. ............... 530/300

\* cited by examiner

*Primary Examiner* — Agnieszka Boesen
(74) *Attorney, Agent, or Firm* — Osha Liang LLP (57) ABSTRACT

Minimal Motifs of linear B-cell epitopes in L1 structure protein from human papillomavirus type 58 (HPV 58) and their applications are disclosed. Eighteen linear epitope motifs and their extended 8-mer peptides in the L1 protein from HPV 58 are described, which can be used as antigens separately or in combination to specifically detect the serum from subjects with HPV 58 infection, or to develop preventive or therapeutic multi-epitope peptide vaccines against HPV 58 by inducing humoral immunity. Of the eighteen B-cell epitope motifs, ten of them are 100% conservative and one is highly conservative among many homologous proteins of high-risk HPVs. They can be used as candidate "universal" epitopes to develop preventive or therapeutic HPV vaccines. The amino acid sequences of the epitope motifs and the 8-mer peptide formula of the invention are shown below in SEQ ID No. 1-2, 2B, 3, 3B, 4-18, 18B, 19, 19B, and 20-32.

7 Claims, 2 Drawing Sheets

Figure 1

Figure 2

MINIMAL MOTIFS OF LINEAR B-CELL EPITOPES IN L1 PROTEIN FROM HUMAN PAPILLOMAVIRUS TYPE 58 AND THEIR APPLICATIONS

FIELD OF THE INVENTION

This invention relates to the field of bio-medicine and biological testing or detection. Specifically, it relates to the identification of the complete set of linear B-cell epitopes in the main capsid protein L1 from HPV 58, and their epitope motifs as well as their applications in preparing vaccines and testing kits for HPV58.

BACKGROUND OF THE INVENTION

Chemical synthesized peptides were expected to be the third milestone, following inactivated virus vaccines and virus subunit vaccines, in the history of human vaccine development. However, none of preventative or therapeutic synthetic peptide vaccines comprising one or two epitopes (epitope is the part of an antigen that is recognized by the immune system, specifically by antibodies and B cells. See the definition in the DETAILED DESCRIPTION OF THE INVENTION) have been approved for clinical applications since 1970s due to the lack of sufficient and efficient immune effects against viruses. Therefore, in order to achieve sufficient and efficient preventive effects against viruses for clinical applications, synthetic peptide vaccines should combine more linear B-cell epitopes if possible (multi-epitope peptide immunogen can be prepared with bioengineering). In addition, single-epitope peptides consisting of 12~20 amino acids are usually used as antigen reagents to detect serum antibodies for the diagnosis of virus infections because natural virus proteins are usually unavailable.

It has been known that a linear B-cell epitope usually consists of 3~8 amino acids. Therefore, it is obvious that using a longer peptide as testing antigen could have problems because it might contain additional epitopes that are recognized by specific antibodies among thousands of antibodies that are present in normal human serum, resulting in high false positive detection rates. In order to improve the specificity and sensitivity of the epitope peptide antigens in diagnosing virus infections and autoimmune diseases, a new trend has been to use short epitope peptides based on minimal motifs, and/or to develop a multi-epitope peptide antigen comprising as many precise epitope motifs as possible on a specific target antigen protein. The former strategy could avoid false positive results, and the rafter will improve detection sensitivity since multiple epitopes in a target protein would be recognized by more antibodies, and this strategy is particularly useful for detecting lower antibody titers elicited by viral infections or autoimmune diseases.

In addition, using the short epitope peptides based on precise motifs also will improve the effectiveness of making monoclonal or polyclonal antibodies for the development of therapeutic biologics or detection agents. Obviously, whether these goals can be achieved by using short epitope peptides or multi-epitope peptides to develop detection antigen, vaccines or therapeutic biologics, will first depend on the identification of a complete set of linear B-cell epitopes and their precise motifs in a target antigen protein.

A large amount of research data demonstrated that cervical cancer, which ranks 2nd globally in the death rates of female cancers, is 90% related to persisted infection at the epidermal of gynecological tract with high-risk (HR-) HPV subtypes, such as HPV 16, 18, 31 and 45 (1). Currently, two pharmaceutical companies (Merck in the U.S. and GlaxoSmithKline (GSK) in UK] have developed preventative HPV vaccines that comprise L1 proteins of HPV 6, 11, 16 and 18, and L1 protein of HPV 16 and 18-L1 proteins, respectively. Even though much research has been done in developing HPV peptide vaccines, there is no report of market approval regarding these peptide vaccines.

Because most women infected by HPV can usually automatically eliminate the infected HPV, and only those, who are continuously infected by HPV, will resulted in cervical cancer, it becomes very important to develop inexpensive and convenient serum detection for HPV infection. Obviously, screening with such detection kits has great significance because such screening can determine who are the objects of vaccination with specific preventative or therapeutic HPV vaccines and what types of specific HPV vaccines should be used. Because of the limitations of early methodologies for epitope identification, it is almost impossible to identify a complete set of linear epitopes (particularly their minimal motifs) on a target protein. Identification of such epitopes or their minimal motifs can improve the detection accuracy, avoiding cross reactions with one or some of thousands of antibodies against unknown antigens present in normal human serum. Currently, no sensitive specific serological detection method for HPV infection has been established, even though in the early time, HPV-infected serum was used to identify specific markers for serological detection of HPV infections (2-5).

HPV 58 is one of the high-risk (HR)-HPVs after HPV 16 and 18 (6). Recent research also demonstrated that high positive detection rates for HPV 58 have been shown in cervical cancer patients in many areas of China including Jiangxi, Shanghai, Hebei, Shanxi, Beijing, Hong Kong and Taiwan (7-15). In some areas of China the detection rates for HPV 58 is even higher than those for HPV18 and only secondary to HPV16 (16-17).

SUMMARY OF THE INVENTION

In view of the stated facts that the HR-HPV 58 is highly epidemic in many areas of China, and that the research on identifying linear B-cell epitopes of HPV 58-L1 protein has not been conducted both in China and abroad, we made efforts in order to develop preventative or therapeutic multi-epitope peptide vaccines against HPV 58 and to develop detection kits using multi-epitope peptide as antigen for HPV58 infection. We used $E.\ coli$ to express HPV58-L1N$^{36\text{-}233}$ and -L1C$^{226\text{-}524}$ proteins (having overlaps each other by 8 residues), and prepared rabbit sera against recombinant (r-) L1N and r-L1C protein, respectively. We also employed the biosynthetic peptide method improved by us (18-19) in epitope mapping of L1 protein from HPV 58. Finally, we conducted a complete and fine mapping of linear B-cell epitopes and their minimal motifs on L1 capsid protein of HPV 58.

Some embodiments of the invention relate to minimal motifs of linear B-cell epitopes in L1 protein from HPV 58. These motifs have the amino acid sequences listed below:
SEQ ID NO: 1: YLPPVP, labeled as HPV58/L1-1$^{38\text{-}43}$; or
SEQ ID NO: 2: PNKFGP, labeled as HPV58/L1-2$^{107\text{-}112}$; or
SEQ ID NO: 33: GHPYLN, labeled as HPV58/L1-2B$^{146\text{-}151}$; or
SEQ ID NO: 3: DDTE, labeled as HPV58/L1-3$^{154\text{-}157}$; or
SEQ ID NO: 34: YPAQPGS, labeled as HPV58/L1-3B$^{162\text{-}168}$; or
SEQ ID NO: 4: ATDC, labeled as HPV58/L1-4$^{208\text{-}211}$; or
SEQ ID NO: 5: PLELF, labeled as HPV58/L1-5$^{213\text{-}217}$; or SEQ ID NO: 6: EDGDMV, labeled as HPV58/L1-6$^{222-227}$; or
SEQ ID NO: 7: DTGF, labeled as HPV58/L1-7$^{228-231}$; or
SEQ ID NO: 8: FGTLQAN, labeled as HPV58/L1-8$^{236-242}$; or
SEQ ID NO: 9: DVPID, labeled as HPV58/L1-9$^{245-249}$; or
SEQ ID NO: 10: PDDL, labeled as HPV58/L1-10$^{298-301}$; or
SEQ ID NO: 11: QLFNK, labeled as HPV58/L1-11$^{331-335}$; or
SEQ ID NO: 12: GTYK, labeled as HPV58/L1-12$^{378-381}$; or
SEQ ID NO: 13: DNFKEY, labeled as HPV58/L1-13$^{383-388}$; or
SEQ ID NO: 14: KEDP, labeled as HPV58/L1-14$^{462-465}$; or
SEQ ID NO: 15: KAKPRLK, labeled as HPV58/L1-15$^{500-506}$; or
SEQ ID NO: 16: SAP, labeled as HPV58/L1-16$^{508-510}$.

Some embodiments of the invention relate to peptides (e.g., 8-mer peptides) containing the minimal motifs described above. For example, such peptides may comprise any of the amino acid sequences listed below:

SEQ ID NO: 17: $X_1$YLPPVPX$_2$ (labeled as L1-1; both $X_1$ and $X_2$ represent V); or
SEQ ID NO: 18: $X_1$PNKFGPX$_2$ (labeled as L1-2; $X_1$ represents D while $X_2$ represents P); or
SEQ ID NO: 35: $X_1$GHPYLNX$_2$ (labeled as L1-2B; $X_1$ represents S while $X_2$ represents K); or
SEQ ID NO: 19: $X_1X_2$DDTEX$_3X_4$ (labeled as L1-3; $X_1$ represents K and $X_2$ represents F while $X_3$ represents T and $X_4$ represents S); or
SEQ ID NO: 36: $X_1$ YPAQPGS (labeled as L1-3B; $X_1$ represents R); or
SEQ ID NO: 20: $X_1X_2$ATDCX$_3X_4$ (labeled as L1-4; both $X_1$ and $X_2$ represent A while both $X_3$ and $X_4$ represent P); or
SEQ ID NO: 21: $X_1$PLELFX$_2X_3$ (labeled as L1-5; $X_1$ represents P and $X_2$ represents N while $X_3$ represents S); or
SEQ ID NO: 22: $X_1$EDGDMVX$_2$ (labeled as L1-6; $X_1$ represents I while $X_2$ represents D); or
SEQ ID NO: 23: $X_1X_2$DTGFX$_3X_4$ (labeled as L1-7; $X_1$ represents M and $X_2$ represents V while $X_3$ represents G and $X_4$ represents C); or
SEQ ID NO: 24: $X_1$FGTLQAN (labeled as L1-8; $X_1$ represents D); or
SEQ ID NO: 25: $X_1X_2$DVPIDX$_3$ (labeled as L1-9; $X_1$ represents K and $X_2$ represents S while $X_3$ represents I); or
SEQ ID NO: 26: $X_1X_2$PDDLX$_3X_4$ (labeled as L1-10; $X_1$ represents A and $X_2$ represents V while $X_3$ represents Y and $X_4$ represents I); or
SEQ ID NO: 27: $X_1X_2$QLFNKX$_3$ (labeled as L1-11; $X_1$ represents E and $X_2$ represents S while $X_3$ represents P); or
SEQ ID NO: 28: $X_1X_2$GTYKX$_3X_4$ (labeled as L1-12; $X_1$ represents K and $X_2$ represents E while $X_3$ represents N and $X_4$ represents D); or
SEQ ID NO: 29: $X_1$DNFKEYX$_2$ (labeled as L1-13; $X_1$ represents N while $X_2$ represents V); or
SEQ ID NO: 30: $X_1X_2$KEDPX$_3X_4$ (labeled as L1-14; $X_1$ represents K and $X_2$ represents E while $X_3$ represents L and $X_4$ represents N); or
SEQ ID NO: 31: $X_1$KAKPRLK (labeled as L1-15; $X_1$ represents L); or
SEQ ID NO: 32: $X_1X_2X_3$SAPX$_4X_5$ (labeled as L1-16; $X_1$ represents L; $X_2$ represents K and $X_3$ represents R while both $X_4$ and $X_5$ represents T),
wherein $X_1$, $X_2$, $X_3$, $X_4$, and $X_5$ each represent a specific amino acid residue noted above.

In some embodiments, $X_1$, $X_2$, $X_3$, $X_4$, and $X_5$ each can be deleted or be kept or be replaced by (substituted with) another residue. Preferred substitutions are homologous substitutions, wherein amino acids of similar properties are substituted. These changes can be made when the minimal motifs or the 8-mer peptides containing each minimal motif are prepared by chemical synthesis as single peptides or by expression as peptides, e.g., fused with GST188 or with other vector proteins.

A synthetic peptide of the invention may contain a suitable length for the intended purpose, such as 5-8 amino acid residues, 6-10 amino acid residues, 8-15 amino acid residues, 10-20 amino acid residues, 10-30 amino acid residues, or the like. In this description, any numeric range is intended to include each individual number within the range as if they are explicitly described. These synthetic peptides may be referred to as "isolated peptides." The term "isolated peptide" is used herein to denote that the peptide is not contained in its nature protein or is not in natural occurrence.

The epitope minimal motifs in L1 protein from HPV 58 described above can be used to develop preventative and/or therapeutic multi-epitope peptide vaccines or biologics against HPV 58. For example, peptides containing these motifs may be used to immunize individuals or to produce antibodies for diagnostic or therapeutic uses.

The epitope minimal motifs in L1 protein from HPV 58 described above can be used as marker antigen(s) to develop detective kits for HPV 58. They can be synthesized as a single peptide, which may contain one or more motifs, or can be expressed biologically either as a single peptide fused with a suitable protein (e.g., GST188 or with other vector protein), or as multi-epitope peptide antigens.

The peptides each containing an epitope minimal motif in the L1 protein of from HPV 58 described above can be used to develop preventative and/or therapeutic multi-epitope peptide vaccines or biologics against HPV 58. The peptides each containing an epitope minimal motif in the L1 protein of HPV 58 described above can be used as marker antigen(s) to develop detective kits for HPV 58. They can be synthesized as a single peptide or can be expressed biologically either as a single peptide fused with a suitable protein (e.g., GST188 or with other vector protein), or as multi-epitope peptide antigens.

Of the eighteen fepitope motifs in this invention, ten are 100% conservative epitope motifs and one is a highly conservative epitope motif among homologous proteins of HR-HPVs. They can be used as candidate epitope peptides to develop "universal" preventative and/or therapeutic multi-epitope peptide vaccines against different types of HPVs. These motifs are listed as below:

SEQ ID NO: 1: HPV58/L1-1$^{38-43}$(YLPPVP);
SEQ ID NO: 2: HPV58/L1-2$^{107-112}$(PNKFGF);
SEQ ID NO: 3: HPV58/L1-3$^{154-157}$ (DDTE);
SEQ ID NO: 6: HPV58/L1-6$^{222-227}$ (EDGDMV);
SEQ ID NO: 7: HPV58/L1-7$^{228-231}$ (DTGF);
SEQ ID NO: 9: HPV58/L1-9$^{245-249}$ (DVPID);
SEQ ID NO: 10: HPV58/L1-10$^{298-301}$ (PDDL);
SEQ ID NO: 11: HPV58/L1-11$^{331-335}$ (QLFNK);
SEQ ID NO: 14: HPV58/L1-14$^{462-465}$ (KEDP);
SEQ ID NO: 16: HPV58/L1-16$^{508-510}$ (SAP).
SEQ ID NO: 5: HPV58/L1-5$^{213-217}$ (PLELF) (expressed as PLELX, X is an alternative amino acid residue)

BRIEF DESCRIPTION OF THE DRAWINGS

FIGS. 1B and 1D: the mapping results of P1-P60 using pre-immune rabbit serum. Arrows in FIG. 1A, C and D indicated that the reactive 18-mer peptide fused with GST188 and positive control (HPV58/E6-1$3^{73-87}$ fused with GST188) can be recognized by pre-immune rabbit serum.

DETAILED DESCRIPTION OF THE INVENTION

This invention relates to eighteen B-cell epitope minimal motifs in the L1 protein from HPV 58 and their extended peptides each containing one of the epitope motifs. The purpose of this invention is to use these epitope motifs and their extended peptides to develop diagnostic kits of HPV 58 infection and therapeutic or preventive vaccines against HPV 58.

Definitions

All scientific and technical terms used in this application have meanings commonly used in the art unless otherwise specified. As used in this application, the following words or phrases have the meanings specified.

As used herein, "epitope" means a molecular region on the surface of an antigen capable of eliciting an immune response and of binding the specific antibody produced by such a response.

As used herein, "minimal motif" means the least or precise immunogenic contiguous amino acid sequence of a linear epitope peptide, capable of eliciting an immune response and of binding the specific antibody produced by such a response. Deletion of part or whole of this contiguous amino acid sequence results in radical or complete loss of capability of eliciting an immune response and of binding the specific antibody produced by such a response.

As used herein, human papillomavirus 58 (HPV 58) is a subtype of human papillomavirus (HPV) with which an infected human female will have high risk of cervical cancer occurrence.

As used herein, "antibody recognition" means the ability of an antibody to bind a specific epitope, peptide, or antigen.

As used herein, "immunogenic" means the ability of an agent to elicit an immune response.

As used herein, "vaccine" means a preparation comprising one or more than one epitope, peptide, or antigen that, when administered, produces or artificially increases immunity to a particular condition. The condition can be, for example, the infection of HPV 58.

As used herein, "adjuvant" means a substance that enhances the immune response to an epitope, peptide, or antigen.

As used herein, "fusion protein" means a protein resulting from the expression of a nucleotide sequence that normally would encode at least a portion of two distinct proteins or peptides.

As used herein, "pharmaceutically acceptable carrier" means a material which is combined with a compound of the invention to facilitate transfer or administration of the compound, but which does not preclude its biological activity. Examples include, but are not limited to, standard pharmaceutical carriers such as phosphate buffered saline (PBS), solution, water, emulsions such as oil/water emulsions, and various types of wetting agents. Additional carriers are liposomes, polymer compositions, and the like. Compositions comprising such carriers are formulated by well-known conventional methods (Remington's Pharmaceutical Sciences, Chapter 43, 14th Ed., Mack Publishing Co., Easton, Pa.).

As used herein, "effective dose" means an amount of an agent that will prevent or eliminate HPVs from the infected subjects.

As used herein, "inducing antibodies" means that the antibody titer, for example of anti-HPV 58 antibodies, is higher after induction than before induction.

The Minimal Motifs of the B-Cell Epitopes in L1 Protein from HPV 58

This invention provides eighteen of minimal motifs of B-cell epitopes in the L1 protein from HPV 58. The amino acid sequences of these epitope motifs are listed as below:

SEQ ID NO: 1: YLPPVP, labeled as HPV58/L1-$1^{38-43}$ in P1;

SEQ ID NO: 2: PNKFGP, labeled as HPV58/L1-$2^{107-112}$ shared by P9 and P10;

SEQ ID NO: 33: GHPYLN, labeled as HPV58/L1-2$B^{146-151}$ in P14;

SEQ ID NO: 3: DDTE, labeled as HPV58/L1-$3^{154-157}$ in P15;

SEQ ID NO: 34: YPAQPGS, labeled as HPV58/L1-3$B^{162-168}$ in P16;

SEQ ID NO: 4: ATDC, labeled as HPV58/L1-$4^{208-211}$ shared by P21 and P22;

SEQ ID NO: 5: PLELF, labeled as HPV58/L1-$5^{213-217}$ shared by P22 and P23;

SEQ ID NO: 6: EDGDMV, labeled as HPV58/L1-$6^{222-227}$ shared by P23 and P24;

SEQ ID NO: 7: DTGF; labeled as HPV58/L1-$7^{228-231}$ shared by P24 and P25;

SEQ ID NO: 8: FGTLQAN; labeled as HPV58/L1-$8^{236-242}$ shared by P25 and P26;

SEQ ID NO: 9: DVPID, labeled as HPV58/L1-$9^{245-249}$ shared by P26 and P27;

SEQ ID NO: 10: PDDL, labeled as HPV58/L1-$10^{298-301}$ shared by P33 and P34;

SEQ ID NO: 11: QLFNK, labeled as HPV58/L1-$11^{331-335}$ shared by P37 and P38;

SEQ ID NO: 12: GTYK, labeled as HPV58/L1-$12^{378-381}$ shared by P43 and P44;

SEQ ID NO: 13: DNFKEY, labeled as HPV58/L1-$13^{383-388}$ in P44;

SEQ ID NO: 14: KEDP, labeled as HPV58/L1-$14^{462-465}$ shared by P53 and P54;

SEQ ID NO: 15: KAKPRLK, labeled as HPV58/L1-$15^{500-506}$ in P59;

SEQ ID NO: 16: SAP, labeled as HPV58/L1-$16^{508-510}$ shared by P59 and P60.

P1~P60 described above represent biosynthetic 18-mer peptides overlapping each other by 10 residues and covering the L1 sequence$^{36-524}$ of HPV 58 (see Experimental Methods). The superscript numbers for each epitope motif (example: the number 38 in HPV58/L-$1^{38-43}$) used in this application indicate their positions in the amino acid sequence of L1 protein from HPV 58. All amino acids in this description are expressed in conventional abbreviations. The correspondence between amino acids and their abbreviations are shown in Table 1.

TABLE 1

| Amino acid | Abbreviation | Amino acid | Abbreviation |
|---|---|---|---|
| Alanine | A | Threonine | T |
| Valine | V | Cysteine | C |
| Leucine | L | Tyrosine | Y |
| Isoleucine | I | Asparagine | N |
| Phenylalanine | F | Glutamine | Q |
| Tryptophane | W | Histidine | H |
| Methionine | M | Lysine | K |
| Proline | P | Argnine | R |
| Glycine | G | Aspartic acid | D |
| Serine | S | Glutamic acid | E |

The Amino Acid Sequences of the 8-Mer Peptides Each Extended from One of the Epitope Motifs in L1 Protein from HPV 58

This invention relates to peptides containing the epitope motifs described above. Some embodiments of the invention relate to peptides (which may be of any suitable length for the intended purpose) containing extended 8-mer peptides, each containing one of the epitope motifs described above. The amino acid sequences of these peptides are listed as below:

SEQ ID NO: 17: $X_1$YLPPVP$X_2$ (both $X_1$ and $X_2$ represent V), labeled as L1-1 and extended from HPV58/L1-1$^{38-43}$;

SEQ ID NO: 18: $X_1$PNKFGP$X_2$ ($X_2$ represents D while $X_2$ represents P), labeled as L1-2 and extended from HPV58/L1-2$^{107-112}$;

SEQ ID NO: 35: $X_1$ GHPYLN $X_2$ ($X_1$ represents S while $X_2$ represents K), labeled as L1-2B and extended from HPV58/L1-2$^{107-112}$;

SEQ ID NO: 19: $X_1X_2$DDTE$X_3X_4$, ($X_1$ represents K and $X_2$ represents F while $X_3$ represents T and $X_4$ represents S), labeled as L1-3 and extended from HPV58/L1-3$^{154-157}$;

SEQ ID NO: 36: $X_1$ YPAQPGS ($X_1$ represents R), labeled as L1-3B and extended from HPV58/L1-2$^{107-112}$.

SEQ ID NO: 20: $X_1X_2$ATDC$X_3X_4$ (Both $X_1$ and $X_2$ represent A while both $X_3$ and $X_4$ represent P), labeled as L1-4 and extended from HPV58/L1-4$^{208-211}$;

SEQ ID NO: 21: $X_1$PLELF$X_2X_3$ ($X_1$ represents P and $X_2$ represents N while $X_3$ represents S), labeled as L1-5 and extended from HPV58/L1-5$^{213-217}$;

SEQ ID NO: 22: $X_1$EDGDMV$X_2$ ($X_1$ represents I while $X_2$ represents D), labeled as L1-6 and extended from HPV58/L1-6$^{222-227}$;

SEQ ID NO: 23: $X_1X_2$DTGF$X_3X_4$ ($X_1$ represents M and $X_2$ represents V while $X_3$ represents G and $X_4$ represents C), labeled as L1-7 and extended from HPV58/L1-7$^{228-231}$;

SEQ ID NO: 24: $X_1$FGTLQAN ($X_1$ represents D), labeled as L1-8 and extended from HPV58/L1-8$^{236-242}$;

SEQ ID NO: 25: $X_1X_2$DVPID$X_3$ ($X_1$ represents K and $X_2$ represents S while $X_3$ represents I), labeled as L1-9 and extended from HPV58/L1-9$^{245-249}$;

SEQ ID NO: 26: $X_1X_2$PDDL$X_3X_4$ ($X_1$ represents A and $X_2$ represents V while $X_3$ represents Y and $X_4$ represents I), labeled as L1-10 and extended from HPV58/L1-10$^{298-301}$;

SEQ ID NO: 27: $X_1X_2$QLFNK$X_3$ ($_3$ ($X_1$ represents E and $X_2$ represents S while $X_3$ represents P), labeled as L1-11 and extended from HPV58/L1-11$^{331-335}$;

SEQ ID NO: 28: $X_1X_2$GTYK$X_3X_4$ ($X_1$ represents K and $X_2$ represents E while $X_3$ represents N and $X_4$ represents D), labeled as L1-12 and extended from HPV58/L1-12$^{378-381}$;

SEQ ID NO: 29: $X_1$DNFKEY$X_2$ ($X_1$ represents N while $X_2$ represents V), labeled as L1-13 and extended from HPV58/L1-13$^{383-388}$;

SEQ ID NO: 30: $X_1X_2$KEDP$X_3X_4$ ($X_1$ represents K and $X_2$ represents E while $X_3$ represents L and $X_4$ represents N), labeled as L1-14 and extended from HPV58/L1-14$^{462-465}$;

SEQ ID NO: 31: $X_1$KAKPRLK ($X_1$ represents L), labeled as L1-15 and extended from HPV58/L1-15$^{500-506}$;

SEQ ID NO: 32: $X_1X_2X_3$SAP$X_4X_5$ ($X_1$ represents L; $X_2$ represents K and $X_3$ represents R while both $X_4$ and $X_5$ represents T), labeled as L1-16 and extended from HPV58/L1-16$^{508-510}$.

For the amino acid sequences above, the character X with a subscript represents a specific amino acid residue, which can be deleted or be kept or be replaced by another residue. These changes can be made when the minimal motifs or the 8-mer peptides containing each minimal motif are prepared by chemical synthesis as a single peptide or by expression as peptides fused with a suitable protein, such as GST188 or other vector proteins.

This invention provides eighteen of B-cell epitope (BCE) motifs in the L1 protein from HPV 58 that are identified for the first time by the inventors. The invention also provides eighteen of their extended 8-mer peptides that can be chemically synthesized or bio-expressed as a short peptide fused with a truncated GST188 or other proteins. These epitope motif peptides can be used alone or in combination in developing preventive or therapeutic HPV multi-epitope peptide vaccines. Moreover, the above-mentioned epitope motif peptides or multi-epitope peptides constructed by bioengineering, can be used as antigens to detect the antibodies against HPV58-L1 protein in the sera from patients with HPV 58 infection.

In addition, of the eighteen epitope motifs we identified, ten motifs are 100% conserved and one is highly conserved among some HR- and low-risk (LR-) HPVs through homologous protein sequence comparison. This discovery indicates that single epitope or multi-epitope peptide vaccines containing these conservative epitopes will have certain degrees of cross-protections from some HR-HPVs listed below:

HPV58/L1-1$^{38-43}$(YLPPVP) versus HPV16/L1$^{38-43}$, HPV31/L1$^{12-17}$ and HPV33/L1$^{12-17}$;

HPV58/L1-2$^{107-112}$ (PNKFGF) versus HPV31/L1$^{81-86}$ with HPV73/L1$^{78-83}$;

HPV58/L1-3$^{154-157}$ (DOTE) versus HPV16/L1$^{153-156}$, HPV18/L1$^{188-191}$, HPV30/L1$^{134-137}$, HPV31/L1$^{128-131}$, HPV33/L1$^{128-131}$, HPV39/L1$^{127-130}$ and HPV73/L1$^{125-128}$;

HPV58/L1-6$^{222-227}$ (EDGDMV) versus HPV18/L1$^{257-262}$, HPV33/L1$^{196-201}$ and HPV45/L1$^{223-228}$;

HPV58/L1-7$^{228-231}$ (DTGF) versus HPV31/L1$^{203-206}$ HPV33/L1$^{202-205}$ and low risky HPV6b/L1$^{198-201}$;

HPV58/L1-9$^{245-249}$ (DVPID) versus HPV33/L1$^{219-233}$, HPV73/L1$^{217-221}$ and low risky HPV6b/L1$^{215-209}$;

HPV58/L1-10$^{298-301}$ (PDDL) versus HPV16/L1$^{298-301}$, HPV33/L1$^{272-275}$ and HPV73/L1$^{270-273}$;

HPV58/L1-11$^{331-335}$ (QLFNK) versus HPV18/L1$^{366-371}$, HPV30/L1$^{312-316}$, HPV33/L1$^{305-310}$, HPV45/L1$^{334-339}$ and low risky HPV6b/L1$^{301-305}$;

HPV58/L1-14$^{462-465}$ (KEDP) versus HPV30/L1$^{443-446}$; HPV31/L1$^{438-441}$ and HPV33/L1$^{436-439}$;

HPV58/L1-16$^{508-510}$ (SAP) versus HPV18/L1$^{548-550}$, HPV30/L1$^{184-186/492-494}$ and HPV31/L1$^{487-489}$.

HPV58/L1-5$^{213-217}$ (PLELF) is a highly conserved epitope (expressed as PLELX, X is an alternative amino acid residue) among HR-HPVs which can be seen in HPV16/L1$^{213-217}$, HPV18/L1$^{248-252}$, HPV30/L1$^{194-198}$, HPV31/L1$^{188-192}$, HPV33/L1$^{187-191}$, HPV39/L1$^{186-190}$, HPV45/L1$^{214-218}$ and HPV73/L1$^{185-189}$. All the expressed 8-mer peptides (-GST188) that contain the motif PLELX in L1 protein from above HR-HPVs can be recognized by rabbit serum raised against HPV 58-L1N.

Meanwhile, the following sequences are the B-cell epitopes specific for the L1 protein of HPV58, and can be used alone or in combination as epitope peptide markers for serological detection of HPV58 infection. These sequences are HPV58/L1-2B (GHPYLN$^{146-151}$), -3B (YPAQPGS$^{162-168}$), -4 (ATDC$^{208-211}$), -8 (FGTLQAM$^{236-242}$), -12 (GTYK$^{378-381}$), -13 (DNFKEY$^{383-388}$) and -15 (KAKPRLK$^{500-506}$).

While the above description refers to minimal motifs and 8-mer peptides, one skilled in the art would know that these motifs or peptides may be contained in a longer peptide or protein (e.g., fusion proteins) for the intended use (immunization, diagnosis, or therapeutic uses). In addition, such motifs or peptides may be coupled to other moieties, such as other organic ligands.

Some embodiments of the invention relate to the use of these peptides or motifs. Some exemplary uses may include preventive use (as immunogens) or therapeutic uses. For therapeutic uses, these peptides may be used to generate monoclonal or polyclonal antibodies. Similarly, thess peptides and their antibodies may be used in diagnosis. The methods of antibody generation are well known in the art, as well as the methods of using peptides and/or antibodies in diagnosis (e.g., ELISA).

Experimental Methods

This invention can be further described as below:

1. The clone of HPV 58 genome was purchased from commercial resource (20). With regular PCR method, the N terminal and C terminal of full-length HPV58-L1 cDNA were amplified from the HPV 58 genome we purchased and then were reconstructed into pRSET-C fusion expression plasmid. The expressed r-L1N$^{36-233}$ and r-L1C$^{226-524}$ proteins were purified from E. coli, and finally used as antigen to immunize three New Zealand white rabbits to prepare rabbit antisera against r-L1N$^{36-233}$ or r-L1C$^{226-524}$, respectively.

Figure 1:
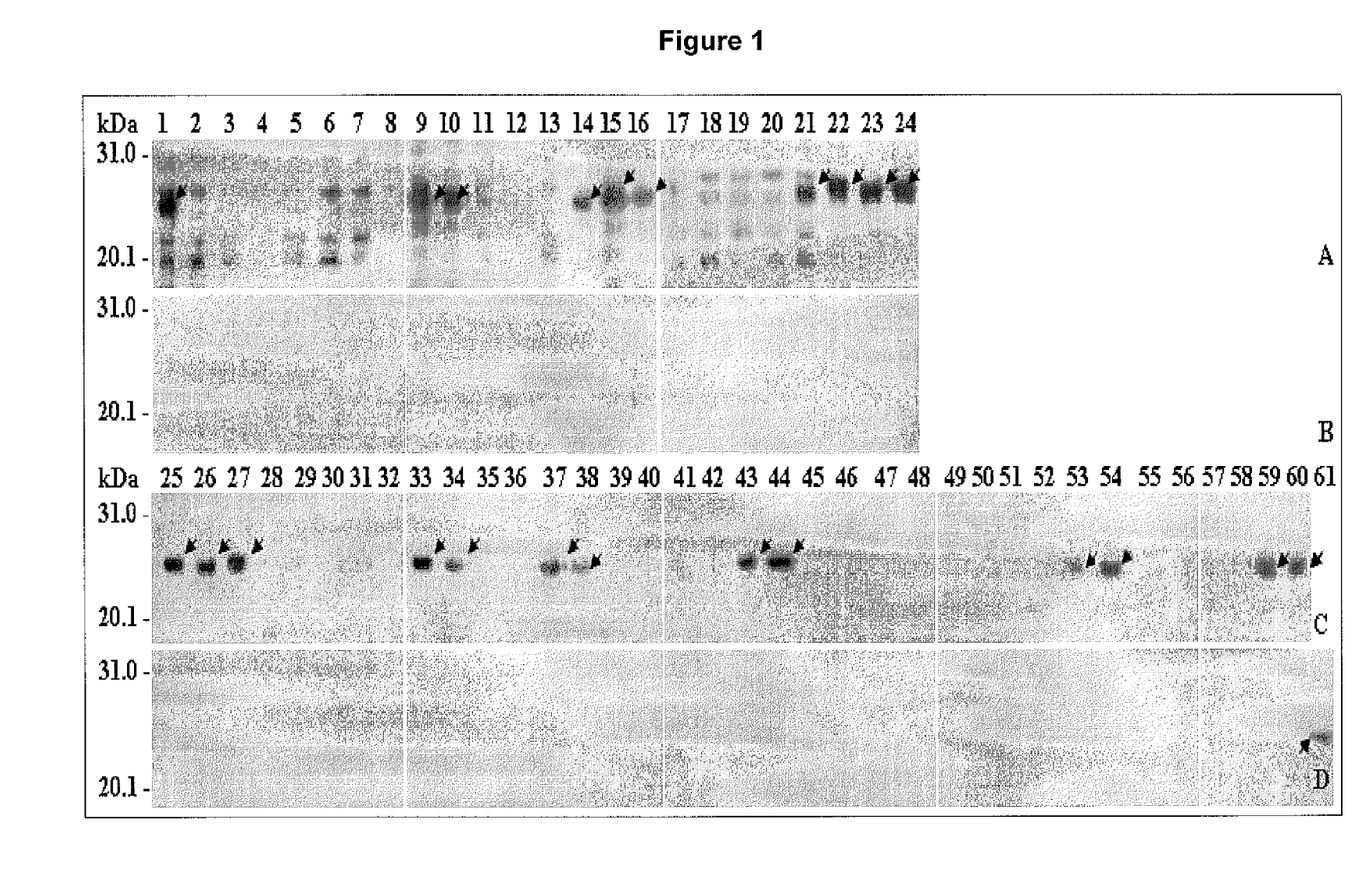
FIG. 1. Mapping of Linear B-Cell Epitopes in L1 Protein from HPV 58 by Western blotting using rabbit serum raised against r-L1N or r-L1C. Lanes 1-24 (A) and lanes 25-60 (C): the 18-mer peptides (fused with GST188) of expressed P1-P60; Lane 61: the 14-mer peptide of positive control.

2. Previously we have constructed a fusion expression plasmid pXXGST-1 specially used for 8/18-mer short peptide biosynthesis in epitope mapping. In this plasmid, the macromolecule protein carrier was a truncated glutathione S-transferases (GST) with 188 residues (GST188) (China Patent NO.: 200710173305.2; 18). DNA recombinant technology was employed to express two sets of 18-mer peptides overlapping each other by 10 residues covering the domains of L1N$^{36-233}$ and L1C$^{226-524}$ fused with GST188, respectively. Specifically the DNA fragments encoding different short peptide were inserted into pXXGST-1 plasmid after annealing of chemically synthesized plus and minus DNA strands to double-strand DNA. The E. coli BL21(DE3) were transformed with recombinant plasmids respectively, and then each positive clone was DNA-sequenced by Shanghai Jierui Biotech Co. Ltd. Each verified clone was used to express a fusion protein containing a target short peptide by thermal induction. As results, a set of 24 short peptide-GST fusion proteins for L1N and a set of 36 short peptide-GST fusion proteins for L1C were prepared. The former set is numbered as P1~P24 (P1~P23 are 18-mer peptides while P24 is a 15-mer peptide), the latter set is numbered as P25~P60 (P25~P59 are 18-mer peptides while P60 is a 19-mer peptide). The expressed P1~P60 fusion proteins were transferred onto nitrocellulose membrane. Epitope mapping of L1 protein was done with rabbit serum raised against r-L1N and r-L1C protein, respectively. As results, there were 10 reactive peptides (P1, P9-P10, P14-P16, P21-P24) for L1N and 13 reactive peptides (P25-P27, P33-P34, P37-P38, P43-P44, P53-P54 and P59-P60) for L1C. The identification was conducted by Western-blotting (FIG. 1).

Each set of 8-mer peptide (fused with GST188, covering each reactive 18-mer peptide and overlapping each other by 7 residues) were further expressed using above mentioned approaches. Each set of 8-mer peptide were named as P61-P71 for P1, P72-P82 for P9, P83-P106 for P14, P15, and P16, P107-P118 for P22, P119-P152 for P24, P25, P26 and P27, P153-163 for P33, P164-P174 for P37, P175-P193 for P43 and P44, P194-P209 for P53 and P54, and P210-P221 for P59 and P60 relative to reactive peptides of P1, P9, P 14, P15, P16, P22 and P24. (If there were two or more neighboring reactive 18-mer peptides, such as P9-P10 and P14-P16, a set of eleven 8-mer peptides of P9 or P14 were usually first expressed for minimal motif mapping. If its fine epitope motif was not within the overlapping sequence of P9 and P10, meaning that the motif was not shared by two neighboring 18-mer peptides, another set of 8-mer peptides of P10 were expressed). Minimal motif mapping of all 8-mer peptide fusion proteins was done using rabbit serum against r-L1N or r-L1C protein.

Figure 2:
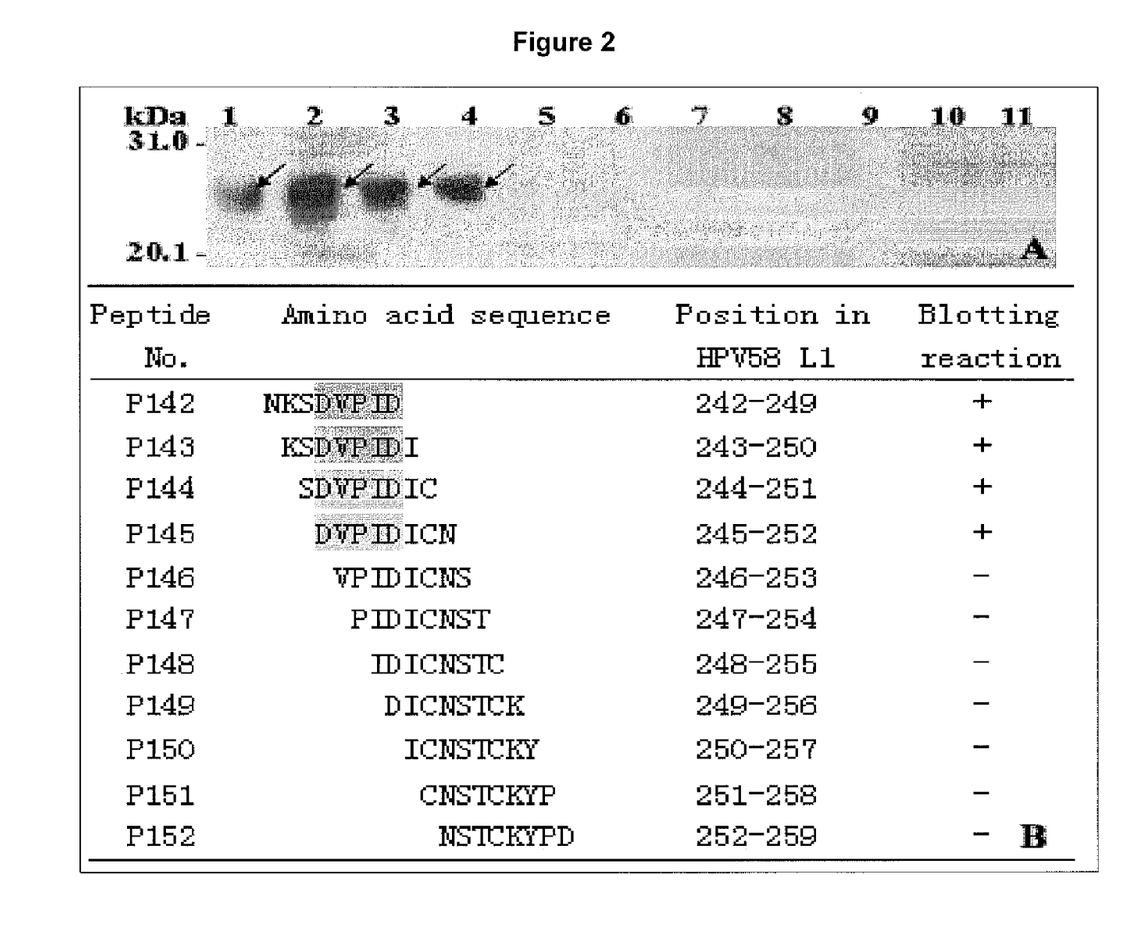
FIG. 2. Mapping the Minimal motif of the reactive epitope peptide P27 (A) and common sequence analysis (B). A: Lanes 1-11: a set of 8-mer peptides (P142-P152) covering the reactive 18-mer peptide P27; B: The figure shows the sequences of 8-mer peptides P142-P52, their position in HPV 58-L1 protein, and a BCE minimal motif identified by Western blotting. The arrows indicated the reactive bands of P142-P145 with Western blotting, respectively; The shaded area indicated the common sequence among the reactive peptides of P142-P145.

The epitope minimal motif was identified according to the common sequence within the neighboring several reactive 8-mer peptides with the fine epitope mapping (see FIG. 2). Finally, eighteen epitope minimal motifs were mapped or identified among twenty-three reactive 18-mer peptides, indicating that there were eighteen B-cell epitopes in the L1 protein from HPV 58. Among these peptides, P1 had only one epitope (YLPPVP$^{38-43}$). P9 and P10 shared a common epitope (PNKFGF$^{107-112}$). P59 had one unique epitope (KAKPRLK$^{500-506}$) and shared one epitope)(ASP$^{508-510}$) with the neighboring P60, and P25 had two epitopes sharing one epitope with the neighboring P24 (DTGF$^{228-231}$) and one with P26(FGTLQAM$^{236-242}$), respectively.

The verification of the eighteen B-cell epitopes in the L1 protein from HPV 58 demonstrated that these minimal motifs and/or their extended 8-mer peptides can be used as candidate peptides for developing preventative HPV58 multi-epitope peptide vaccines. Among them seven of HPV58 specific B-cell epitope peptides as well as their multi-epitope peptides can be used as specific antigen markers to detect HPV58 infection.

EXAMPLES

This invention can be further described with the following examples. These examples do not mean to restrict the scope of the invention as has been completely explained in the description above. For those experimental methods without specifying the conditions were all carried out according to regular conditions and to the protocol of "Molecular Cloning: A Laboratory Manual" [the 3$^{rd}$ edition written by Joe Sambrook and David Russell (USA) and translated by Peitang Huang (Science Press, 2002)] or to the protocol recommended by the manufacturers.

Example 1

Mapping of the Linear B-Cell Epitope in L1 Protein from HPV 58

Materials and Methods:

1. HPV58 genome clone (pLink322/HPV58 plasmid) was purchased from commercial resource. Plasmid pRSET-C was purchased from Invitrogen Inc. in the U.S. The thermo-inducible plasmid pXXGST-1 was constructed by the inventor (China Patent NO.: 200710173305.2). E. Coli BL21(DE3) was purchased from commercial resource.

2. Restriction endonucleases including EcoR I, BamH I, Sal I, Taq polymerase and T4 DNA ligase were purchased from a Japanese company, TaKaRa Biotechnology. Pre-stained protein molecular weight standards and goat anti-rabbit-HRP were purchased from Shanghai Sangon Biotech Co. Ltd. Electrogenerated chemiluminescence (ECL) reagents were purchased from a UK company GE Healthcare. 0.2 um nitrocellulose membrane was purchased from Whatman Gmbn Hahnestr. 6×His monoclonal antibody was purchased from Shanghai Ruixing Biotech Co. Ltd.
3. QIAprep Spin Miniprep Plasmid Extraction Kit, QIAquick PCR Product Purification Kit and quick gel extraction kit were purchased from a German company QIAGEN.
4. New Zealand white rabbits were purchased from Shanghai BK Experimental Animal Co. Ltd.
5. The plus and minus strands of DNA fragments encoding each 8/18-mer peptide were synthesized by Shanghai Jierui Biotech Co. Ltd. All of these synthetic DNAs I had a 'gattc' sequence (BamH I cohesive end) on the 5' end (the plus strand) and a 'taag' sequence (termination codon TAA-Sal I cohesive end) on 3' end (minus strand).
6. In order to obtain rabbit serum against the HPV 58-L1 protein, two DNA fragments encoding $L1N^{36-233}$ and $L1C^{226-524}$ proteins were prepared according to the open information on HPV58-L1 gene sequence (21) and methods in the reference literature (22). The preparation process can be briefly described as below: The encoding genes of $L1N^{36-233}$ and $L1C^{226-524}$ both with BamH I and EcoR I sticky ends were amplified from pLink322/HPV58 plasmid through PCR; The PCR products were inserted into pRSET-C plasmids after digestion using BamH I and Sal I enzymes. The *E. coli* BL21(DE3) were transformed with the recombinant plasmids, and then the positive clones were sent out to conduct DNA sequencing. The verified clones were used to express L1N and L1C protein with 6×His tag, and two expressed proteins were identified using 6×His monoclonal antibodies, respectively. Finally, the purified r-L1N and r-L1C proteins were used to immunize three New Zealand white rabbits and the rabbit antisera were collected after two boosters.

Mapping of the epitopes in the L1 protein from HPV58 with rabbit sera can be specifically described as below:
1. DNAs were designed for encoding two sets of 18-mer peptides overlapping each other by 10 residues and covering $L1N^{36-233}$ and $L1C^{226-524}$. Then the plus and minus strands of DNA fragments encoding each 18 mer peptides (numbered as P1-P60) were synthesized by Shanghai Jierul Biotech Co. Ltd.
2. The complementary DNA fragments at the concentration level of 1or $2OD_{260}$ (optical density at wavelength of 260nm) value were dissolved to 20μmol/μl stock solution with ddH$_2$O (according to the DNA synthesis report); 10μL stock solution and 20μL ddH$_2$O were mixed in a 1.5mL eppendorf tube and then heated at 94° C. for 5mins before cooling to room temperature. In 15μl of the reaction mixture, 2 μL annealing fragments, 1 μL of 200 ng/μL pXXGST-1plasmids digested with BamH I and Sal I, 1μL T4DNA ligase and 1.5μL buffer were mixed and incubated overnight. The ligation solution was transformed into BL21(DE3) host, then the bacteria was smeared on the Luria Broth medium (LB) plates containing ampicillin. After overnight culture at 37° C., the growing colonies (one colony for one clone) on the LB plate were inoculated into 3mL LB culture solution for inducible expression. The expressed GST188-18mer (P1-P60) fusion proteins were analyzed and verified through 15% SDS-PAGE (about 2kDa mobility difference from the control) using GST188protein as control which was expressed with pXXGST-2plasmid. Each recombinant clone was picked and cultured for DNA sequencing.
3. The clones with correct sequencing results were inoculated into 3 mL LB medium containing ampicillin and cultured overnight at 30° C. with shaking. The inoculums (or cultured solution) was inoculated into fresh LB medium containing ampicillin at 1:50 (inoculums:fresh medium) and cultured at 30° C. with shaking for 2~3 hrs until $OD_{600}$ reaches 0.6~0.8. The temperature was up-regulated to 42° C. and then incubated for 4 hr for heat inducing expression. Then the bacteria were harvested by centrifugation, and was added with lysate, and finally was boiled for 5 min for further usage.
4. The total expressed bacteria proteins were separated with 15% SDS-PAGE. After electrophoresis, one gel was stained with Coomassie blue, while the other gel was transferred onto nitrocellulose membrane at 100 mA for 2 hrs. The membrane was stained with ponceaux for 2 mins. Pictures were taken with digital camera before washing off the ponceaux.
5. The membrane was washed with PBS buffer for four times and then blocked with 5% skimmed milk powder overnight. After additional washing with PBS buffer for four times, the membrane was incubated for 2 hrs at room temperature in 8~10 ml reaction solution mixed with 30 μL of the rabbit serum raised against r-L1N or r-L1C protein or with 30 μL of pre-immune rabbit serum. After washing with PBS buffer, the membrane was incubated for 1 hr at room temperature in 10 ml of reaction solution mixed with 5 μL of goat anti rabbit IgG/HRP. Finally the membrane was washed with PBS buffer and then analyzed with electrogenerated chemiluminescence (ECL), exposed to X-film (FIG. 1A-D).
6. As shown in FIG. 1, twenty-three reactive 18-mer peptides in L1 protein from HPV58 were identified using rabbit serum raised against r-L1N or r-L1C protein (FIGS. 1A and 1C). However, no positive bands were seen when using pre-immune rabbit serum as shown in FIGS. 1B and 1C.

Example 2

Mapping of the BCE Minimal Motif of the Reactive Peptide P27

Materials and Methods: (refer to the corresponding parts in Example 1)
1. The reactive peptide P27 shown in Example 1 (as seen in FIG. 1) was taken as an example for mapping the BCE minimal motif of an 18-mer peptide. The plus and minus strands of DNA fragments encoding each 8-mer peptide (numbered as P142-P152) had an overlap of 7 residues each other and covered the whole P27 peptide sequence. The DNAs were synthesized by Shanghai Jierui Biotech Co. Ltd.

Steps 2-4 were the same as steps 2-4 in Example 1.

The membrane was washed with PBS buffer for four times and then blocked with 5% skimmed milk powder overnight. After additional washing with PBS buffer for four times, the membrane was incubated for 2 hrs at room temperature in 8-10 ml of reaction solution mixed with 30 μL of rabbit serum raised against r-L1N (1:200 dilution). After washing with PBS buffer, the membrane was incubated for 1 hr at room temperature in 10 ml of reaction solution mixed with 5 μL of goat anti human IgG/HRP. Finally the membrane was washed with PBS buffer and then analyzed with electrogenerated chemiluminescence (ECL), exposed to X-film (FIG. 2A).

The epitope minimal motif DVPID present in the reactive peptide P27 was identified according to the common sequence shown in four reactive 8-mer peptides (P142-P145, FIG. 2B).

This invention described the identification of eighteen B-cell epitopes and their minimal motifs in the L1 protein from HPV58. The 8-mer peptides or 8-mer peptide fusion proteins each containing a minimal motif can be used alone or in combination to develop preventive and/or therapeutic multi-epitope peptide vaccines against HPV58, or to specifically detect HPV58 infection as antigen peptide(s), which could be prepared either by chemosynthesis or by bio-expression as a multi-epitope peptide fusion protein).

Useful peptides of the invention include amino acid sequences comprising one or more of the minimal motifs or the 8-mer peptides of this invention. Such peptides can be expressed biologically as fusion proteins. The fusion proteins of the invention can include, for example, one or more epitope minimal motif(s) in the L1 protein of HPV 58, fused to one or more T-cell epitope peptides, which may come from HPV or non-HPV immunogens or antigens.

As used herein, "pharmaceutically acceptable carrier" means a material which is combined with a compound of the invention to facilitate transfer or administration of the compound, but which does not preclude its biological activity. Examples include, but are not limited to, standard pharmaceutical carriers such as phosphate buffered saline (PBS), solution, water, emulsions such as oil/water emulsions, and various types of wetting agents. Additional carriers are liposomes, polymer compositions, and the like. Compositions comprising such carriers are formulated by well-known conventional methods (Remington's Pharmaceutical Sciences, Chapter 43, 14th Ed., Mack Publishing Co., Easton, Pa.).

Useful compositions of the invention include one or more peptides and/or fusion proteins of the invention combined with a pharmaceutically acceptable carrier and/or other pharmaceutical additive ingredients. The composition can include an adjuvant capable of enhancing an immune response to the epitope of the peptides or fusion proteins of the invention. Suitable adjuvants are known and include, for example, emulsifiers, Quil A, mineral oil, aluminum hydroxide, aluminum phosphate, etc.

The vaccines of the invention comprise an effective therapeutic dose of the immunogenic HPV epitope peptides sufficient to induce the production of anti-HPV 58-L1 antibodies, thus resulting in a preventive or therapeutic effect. Preferably, the vaccine is effective to produce such an effect in humans.

Nucleic acid sequences of the invention encode the amino acid sequences of the HPV58-L1 epitopes and peptides of the invention, and include both deoxyribo- and ribonucleic acids. The nucleic acid sequences can be included in a vector for expression of the amino acids in a host cell. Vectors suitable for expression are known, and include, but are not limited to, bacterial expression vectors, yeast expression vectors, and baculovirus vectors. The HPV 58-L1's epitopes are expressed in a host cell, when the host cell is cultured under suitable conditions. Host cells can include, but are not limited to, silk worm larvae, CHO cells, *E. coli*, and yeast.

Methods of recovery of peptides expressed in host cells are known. Vectors, hosts, methods of expressing vectors and recovering peptides are known (see, for example, Sambrook et al., Molecular Cloning: A Laboratory Manual, the 3$^{rd}$ edition and translated by Peitang Huang, Science Press, 2002, and O'Reilley et al., Baculovirus Expression Vectors: A Laboratory Manual, Oxford University Press, 1994).

The B-cell epitopes in L1 protein of HPV 58 and their fine motifs of the invention are preferably used to induce anti-HPV 58-L1 antibodies in a host animal. For example, a fusion protein comprising one or more of the amino acid sequence(s) of this invention, with or without T-cell epitopes from HPVs or non-HPV immunogens, is administered to an animal, for example by injection. The immunogen may be delivered with an adjuvant, as known in the field. The course of administration may be one or multiple boosters, as needed to induce anti-HPV antibody titer. Thereafter, maintenance doses can be administered as required to retain a sufficient antibody titer. The appropriate dose and immunization regimen for the peptide, peptide composition, or vaccine of the invention can be determined by one of skill in the art, armed with the information provided in this text and the Examples in this text.

In addition, the minimal motif(s) of the epitope(s) as well as their extended peptide(s) of this invention can be used as antigen alone or in combination to specifically detect the sera from subjects with HPV 58 infection. Since natural virus proteins are not usually available or are very difficult to prepare, the amino acid sequence of the invention can be used to prepare antigen reagent in detecting serum antibodies for the diagnosis of HPV 58 infection, or more types of HPV infection by using the 100% conserved epitope peptides among HR-HPVs of this invention.

The above specification includes numerous citations, publications and texts. Each is here incorporated by reference for all purposes as if fully set forth. The above specification, examples, and data provide a complete description of the manufacture and use of the composition of the invention. Since many embodiments of the invention can be made without departing from the spirit and scope of the invention, the invention resides in the claims hereafter appended. Since the minimal motifs of the B-cell epitopes as well as the extended 8-mer peptides can be modified or changed as needed, the attached claims cover all of the changes in the scope of the invention.

Literature Cited

1. Tovar J M, et al. Human papillomavirus, cervical cancer, and the vaccine. Postgrad. Med. 2008; 120: 79-84.
2. Dillner J, Dillner L, Utter G, et al. Mapping of linear epitopes of human papillomavirus type 16: the L1 and L2 open reading frames. Int. J. Cancer. 1990; 45: 529-535.
3. Dillner J. Mapping of linear epitopes of human papillomavirus type 16: The E1, E2, E4, E6 and E7 open reading frames. Int. J. Cancer. 1990; 46: 703-711.
4. Bleul C, Müller M, Frank R, et al. Human papillomavirus type 18 E6 and E7 antibodies in human sera: increased anti-E7 prevalence in cervical cancer patients. J. Clin. Microbiol. 1991; 29: 1579-1588.
5. Jenison S A, et al. Characterization of human antibody-reactive epitopes encoded by human papillomavirus types 16 and 18. J. Virology. 1991; 65: 1208-1218.
6. Lungu O, et al. A polymerase chain reaction-enzyme-linked immunosorbent assay method for detecting human papillomavirus in cervical carcinomas and high-grade cervical cancer precursors. Obstet. Gynecol. 1995; 85: 337-342.
7. Lin Q Q, Yu S Z, Qu W, Cruz Y, Burk R D. Human papillomavirus types 52 and 58.
1. Int. J. Cancer. 1998; 75: 484-485.
8. Huang S, Afonina A, Miller B A, Beckmann A M. Human papillomavirus types 52 and 58 are prevalent in cervical cancers from Chinese women. Int. J. Cancer. 1997; 70: 408-411.

9. Cai H B, Ding X H, Chen C C. Prevalence of single and multiple human papillomavirus types in cervical cancer and precursor lesions in Hubei, China. Oncology. 2009; 76: 157-161.
10. Dai M, Bao Y P, L1N, et al. Human papillomavirus infection in Shamd Province, People's Republic of China: a population-based study. Br. J. Cancer. 2006; 95:96-101.
11. Gao Y, et al. Detection of HPV 58 and cloning of its E7 gene in cervical cancer. Ch. J. Oncology. 2004; 26: 543-546.
12. Zhao R, et al. Human papillomavirus infection in Beijing, People's Republic of China: a population based study. Br. J. Cancer, 2009; 101: 1635-1640.
13. Lai H C, et al. Favorable clinical outcome of cervical cancers infected with human papilloma virus type 58 and related types. Int. J. Cancer. 1999; 84: 553-557.
14. Chan P K, et al. High prevalence of human papillomavirus type 58 in Chinese women with cervical cancer and pre-cancerous lesions. J. Med. Virol. 1999; 59: 232-238.
15. Bao Y P, et al. Human papillomavirus type-distribution in the cervix of Chinese women: a meta-analysis. Int. J. STD AIDS. 2008; 19: 106-111.
16. Li J, et al. Investigation of human papillomavirus (HPV) infection in cervical carcinoma tissues of Chinese women. Chinese J. Exp. Clin. Virol. 1996; 10: 50-55.
17. Liu B Y, et al. Investigation on relationship between the papillomavirus type58 (HPV58) infection and cervix cancer in China. Chinese J. Exp. Clin. Virol. 1996; 10: 118-121.
18. Xu, et al. Minimal motif mapping of a known epitope on human zona pellucida protein-4 using a peptide biosynthesis strategy. J. Reprod. Immunol. 2009; 81: 9-16.
19. Xu et al. Mapping of minimal motifs of B-cell epitopes on human zona pellucida glycoprotein-3 Clin Dev Immunol. 2012; 2012: 831010. Epub 2011 Nov. 17
20. Kirii Y, et al. Human papillomavirus tye 58 DNA sequence. Virol, 1991; 185: 424-427.
21. Kirii Y, et al. Human papillomavirus type 58 DNA sequence. Virol. 1991; 185: 424-427.
22. Song L, et al. Immunogenicity of recombinant human zona pellucida-3 peptides expressed in *E. coli* and efficacy of their antisera to inhibit in vitro human sperm-egg binding. Acta. Phys. Sin. 2005; 57: 682-688.

What is claimed is:

1. A method for inducing an immune response comprising administering in a subject a composition comprising one or more B-cell epitopes present in HPV 58/L1 protein, wherein one B-cell epitope is a peptide from 4 to 7 amino acid residues in length and comprises a sequence selected from the group consisting of:

YLPPVP (SEQ ID NO: 1) corresponding to amino acids 38-43 of HPV58 L1/1;

PNKFGP (SEQ ID NO: 2) corresponding to amino acids 107-112 of HPV58/L1-2;

GHPYLN (SEQ ID N.33) corresponding to amino acids 146-151 of HPV58/L1-2B;

DDTE (SEQ ID NO: 3) corresponding to amino acids 154-157 of HPV58/L1-3;

YPAQPGS (SEQ ID NO: 34) corresponding to amino acids 162-168 of HPV58/L1-3B;

ATDC (SEQ ID NO: 4) corresponding to amino acids 208-211 of HPV58/LI-4;

PLELF (SEQ ID NO: 5) corresponding to amino acids 213-217 of HPV58/L1-5;

EDGDMV (SEQ ID NO: 6) corresponding to amino acids 222-227 of HPV58/L1-6;

DTGF (SEQ ID NO: 7) corresponding to amino acids 228-231 of HPV58/L1-7;

FGTLQAN (SEQ ID NO: 8) corresponding to amino acids 236-242 of HPV58/L1-8;

DVPID (SEQ ID NO: 9) corresponding to amino acids 245-249 of HPV58/L1-9;

PDDL (SEQ ID NO: 10) corresponding to amino acids 298-301 of HPV58/L1-10;

QLFNK (SEQ ID NO: 11) corresponding to amino acids 331-335 of HPV58/L1-11;

GTYK (SEQ ID NO: 12) corresponding to amino acids 378-381 of HPV58/L1-12;

DNFKEY (SEQ ID NO: 13) corresponding to amino acids 383-388- of HPV58/L1-13;

KEDP (SEQ ID NO: 14) corresponding to amino acids 462-465 of HPV58/L1-14; or

KAKPRLK (SEQ ID NO: 15) corresponding to amino acids 500-506 of HPV58/L1-15.

2. The method of claim 1, wherein the B-cell epitope is fused with a non-HPV58immunogenic or antigenic sequence.

3. The method of claim 1, wherein the B-cell epitope is a peptide of 4, 5, or 6 amino acids in length.

4. The method of claim 1, wherein the B-cell epitope is a peptide of 4 or 5 amino acids in length.

5. The method of claim 1, wherein the composition comprises two or more B cell epitopes as defined in claim 1.

6. The method of claim 5, wherein one of the two B cell epitopes is SEQ ID NO: 1.

7. The method of claim 1, wherein the subject is a human.

* * * * *

UNITED STATES PATENT AND TRADEMARK OFFICE
CERTIFICATE OF CORRECTION

PATENT NO. : 8,715,681 B2  
APPLICATION NO. : 13/364952  
DATED : May 6, 2014  
INVENTOR(S) : Wanxiang Xu et al.

Page 1 of 1

It is certified that error appears in the above-identified patent and that said Letters Patent is hereby corrected as shown below:

On the title page item (73), Assignee "Hengsun Pharmaceutical Technology Co., Ltd., Guangzhou (CN)" should read -- Hengsun Pharmaceutical Technology Co., Ltd., Guangzhou (CN); Riting Liu, Guangzhou (CN) --.

Signed and Sealed this  
Third Day of November, 2015

Michelle K. Lee  
*Director of the United States Patent and Trademark Office*

```
                        SEQUENCE LISTING

<160> NUMBER OF SEQ ID NOS: 36

<210> SEQ ID NO 1
<211> LENGTH: 6
<212> TYPE: PRT
<213> ORGANISM: artificial sequence
<220> FEATURE:
<223> OTHER INFORMATION: HPV58/L1-1 38-43

<400> SEQUENCE: 1

Tyr Leu Pro Pro Val Pro
1               5

<210> SEQ ID NO 2
<211> LENGTH: 6
<212> TYPE: PRT
<213> ORGANISM: artificial sequence
<220> FEATURE:
<223> OTHER INFORMATION: HPV58/L1-2 107-112

<400> SEQUENCE: 2

Pro Asn Lys Phe Gly Pro
1               5

<210> SEQ ID NO 3
<211> LENGTH: 4
<212> TYPE: PRT
<213> ORGANISM: artificial sequence
<220> FEATURE:
<223> OTHER INFORMATION: HPV58/L1-3 154-157

<400> SEQUENCE: 3

Asp Asp Thr Glu
1

<210> SEQ ID NO 4
<211> LENGTH: 4
<212> TYPE: PRT
<213> ORGANISM: artificial sequence
<220> FEATURE:
<223> OTHER INFORMATION: HPV58/L1-4 208-211

<400> SEQUENCE: 4
```

```
Ala Thr Asp Cys
1

<210> SEQ ID NO 5
<211> LENGTH: 5
<212> TYPE: PRT
<213> ORGANISM: artificial sequence
<220> FEATURE:
<223> OTHER INFORMATION: HPV58/L1-5 213-217

<400> SEQUENCE: 5

Pro Leu Glu Leu Phe
1               5

<210> SEQ ID NO 6
<211> LENGTH: 6
<212> TYPE: PRT
<213> ORGANISM: artificial sequence
<220> FEATURE:
<223> OTHER INFORMATION: HPV58/L1-6 222-227

<400> SEQUENCE: 6

Glu Asp Gly Asp Met Val
1               5

<210> SEQ ID NO 7
<211> LENGTH: 4
<212> TYPE: PRT
<213> ORGANISM: artificial sequence
<220> FEATURE:
<223> OTHER INFORMATION: HPV58/L1-7 228-231

<400> SEQUENCE: 7

Asp Thr Gly Phe
1

<210> SEQ ID NO 8
<211> LENGTH: 7
<212> TYPE: PRT
<213> ORGANISM: artificial sequence
<220> FEATURE:
<223> OTHER INFORMATION: HPV58/L1-8 236-242

<400> SEQUENCE: 8

Phe Gly Thr Leu Gln Ala Asn
1               5

<210> SEQ ID NO 9
<211> LENGTH: 5
<212> TYPE: PRT
<213> ORGANISM: artificial sequence
<220> FEATURE:
<223> OTHER INFORMATION: HPV58/L1-9 245-249

<400> SEQUENCE: 9

Asp Val Pro Ile Asp
1               5

<210> SEQ ID NO 10
<211> LENGTH: 4
<212> TYPE: PRT
<213> ORGANISM: artificial sequence
<220> FEATURE:
<223> OTHER INFORMATION: HPV58/L1-10 298-301

<400> SEQUENCE: 10

Pro Asp Asp Leu
```

<210> SEQ ID NO 11
<211> LENGTH: 5
<212> TYPE: PRT
<213> ORGANISM: artificial sequence
<220> FEATURE:
<223> OTHER INFORMATION: HPV58/L1-11 331-335

<400> SEQUENCE: 11

Gln Leu Phe Asn Lys
1               5

<210> SEQ ID NO 12
<211> LENGTH: 4
<212> TYPE: PRT
<213> ORGANISM: artificial sequence
<220> FEATURE:
<223> OTHER INFORMATION: HPV58/L1-12 378-381

<400> SEQUENCE: 12

Gly Thr Tyr Lys
1

<210> SEQ ID NO 13
<211> LENGTH: 6
<212> TYPE: PRT
<213> ORGANISM: artificial sequence
<220> FEATURE:
<223> OTHER INFORMATION: HPV58/L1-13 383-388

<400> SEQUENCE: 13

Asp Asn Phe Lys Glu Tyr
1               5

<210> SEQ ID NO 14
<211> LENGTH: 4
<212> TYPE: PRT
<213> ORGANISM: artificial sequence
<220> FEATURE:
<223> OTHER INFORMATION: HPV58/L1-14 462-465

<400> SEQUENCE: 14

Lys Glu Asp Pro
1

<210> SEQ ID NO 15
<211> LENGTH: 7
<212> TYPE: PRT
<213> ORGANISM: artificial sequence
<220> FEATURE:
<223> OTHER INFORMATION: HPV58/L1-15 500-506

<400> SEQUENCE: 15

Lys Ala Lys Pro Arg Leu Lys
1               5

<210> SEQ ID NO 16
<211> LENGTH: 3
<212> TYPE: PRT
<213> ORGANISM: artificial sequence
<220> FEATURE:
<223> OTHER INFORMATION: HPV58/L1-16 508-510

<400> SEQUENCE: 16

Ser Ala Pro
1

```
<210> SEQ ID NO 17
<211> LENGTH: 8
<212> TYPE: PRT
<213> ORGANISM: artificial sequence
<220> FEATURE:
<223> OTHER INFORMATION: L1-1

<400> SEQUENCE: 17

Val Tyr Leu Pro Pro Val Pro Val
1               5

<210> SEQ ID NO 18
<211> LENGTH: 8
<212> TYPE: PRT
<213> ORGANISM: artificial sequence
<220> FEATURE:
<223> OTHER INFORMATION: L1-2

<400> SEQUENCE: 18

Asp Pro Asn Lys Phe Gly Pro Pro
1               5

<210> SEQ ID NO 19
<211> LENGTH: 8
<212> TYPE: PRT
<213> ORGANISM: artificial sequence
<220> FEATURE:
<223> OTHER INFORMATION: L1-3

<400> SEQUENCE: 19

Lys Phe Asp Asp Thr Glu Thr Ser
1               5

<210> SEQ ID NO 20
<211> LENGTH: 8
<212> TYPE: PRT
<213> ORGANISM: artificial sequence
<220> FEATURE:
<223> OTHER INFORMATION: L1-4

<400> SEQUENCE: 20

Ala Ala Ala Thr Asp Cys Pro Pro
1               5

<210> SEQ ID NO 21
<211> LENGTH: 8
<212> TYPE: PRT
<213> ORGANISM: artificial sequence
<220> FEATURE:
<223> OTHER INFORMATION: L1-5

<400> SEQUENCE: 21

Pro Pro Leu Glu Leu Phe Asn Ser
1               5

<210> SEQ ID NO 22
<211> LENGTH: 8
<212> TYPE: PRT
<213> ORGANISM: artificial sequence
<220> FEATURE:
<223> OTHER INFORMATION: L1-6

<400> SEQUENCE: 22

Ile Glu Asp Gly Asp Met Val Asp
1               5

<210> SEQ ID NO 23
```

```
<211> LENGTH: 8
<212> TYPE: PRT
<213> ORGANISM: artificial sequence
<220> FEATURE:
<223> OTHER INFORMATION: L1-7

<400> SEQUENCE: 23

Met Val Asp Thr Gly Phe Gly Cys
1               5

<210> SEQ ID NO 24
<211> LENGTH: 8
<212> TYPE: PRT
<213> ORGANISM: artificial sequence
<220> FEATURE:
<223> OTHER INFORMATION: L1-8

<400> SEQUENCE: 24

Asp Phe Gly Thr Leu Gln Ala Asn
1               5

<210> SEQ ID NO 25
<211> LENGTH: 8
<212> TYPE: PRT
<213> ORGANISM: artificial sequence
<220> FEATURE:
<223> OTHER INFORMATION: L1-9

<400> SEQUENCE: 25

Lys Ser Asp Val Pro Ile Asp Ile
1               5

<210> SEQ ID NO 26
<211> LENGTH: 8
<212> TYPE: PRT
<213> ORGANISM: artificial sequence
<220> FEATURE:
<223> OTHER INFORMATION: L1-10

<400> SEQUENCE: 26

Ala Val Pro Asp Asp Leu Tyr Ile
1               5

<210> SEQ ID NO 27
<211> LENGTH: 8
<212> TYPE: PRT
<213> ORGANISM: artificial sequence
<220> FEATURE:
<223> OTHER INFORMATION: L1-11

<400> SEQUENCE: 27

Glu Ser Gln Leu Phe Asn Lys Pro
1               5

<210> SEQ ID NO 28
<211> LENGTH: 8
<212> TYPE: PRT
<213> ORGANISM: artificial sequence
<220> FEATURE:
<223> OTHER INFORMATION: L1-12

<400> SEQUENCE: 28

Lys Glu Gly Thr Tyr Lys Asn Asp
1               5

<210> SEQ ID NO 29
<211> LENGTH: 8
<212> TYPE: PRT
```

```
<213> ORGANISM: artificial sequence
<220> FEATURE:
<223> OTHER INFORMATION: L1-13

<400> SEQUENCE: 29

Asn Asp Asn Phe Lys Glu Tyr Val
1               5

<210> SEQ ID NO 30
<211> LENGTH: 8
<212> TYPE: PRT
<213> ORGANISM: artificial sequence
<220> FEATURE:
<223> OTHER INFORMATION: L1-14

<400> SEQUENCE: 30

Lys Glu Lys Glu Asp Pro Leu Asn
1               5

<210> SEQ ID NO 31
<211> LENGTH: 8
<212> TYPE: PRT
<213> ORGANISM: artificial sequence
<220> FEATURE:
<223> OTHER INFORMATION: L1-15

<400> SEQUENCE: 31

Leu Lys Ala Lys Pro Arg Leu Lys
1               5

<210> SEQ ID NO 32
<211> LENGTH: 8
<212> TYPE: PRT
<213> ORGANISM: artificial sequence
<220> FEATURE:
<223> OTHER INFORMATION: L1-16

<400> SEQUENCE: 32

Leu Lys Arg Ser Ala Pro Thr Thr
1               5

<210> SEQ ID NO 33
<211> LENGTH: 6
<212> TYPE: PRT
<213> ORGANISM: artificial sequence
<220> FEATURE:
<223> OTHER INFORMATION: HPV58/L1-2B 146-151

<400> SEQUENCE: 33

Gly His Pro Tyr Leu Asn
1               5

<210> SEQ ID NO 34
<211> LENGTH: 7
<212> TYPE: PRT
<213> ORGANISM: artificial sequence
<220> FEATURE:
<223> OTHER INFORMATION: HPV58/L1-3B 162-168

<400> SEQUENCE: 34

Tyr Pro Ala Gln Pro Gly Ser
1               5

<210> SEQ ID NO 35
<211> LENGTH: 8
<212> TYPE: PRT
<213> ORGANISM: artificial sequence
<220> FEATURE:
```

```
<223> OTHER INFORMATION: L1-2B

<400> SEQUENCE: 35

Ser Gly His Pro Tyr Leu Gln Lys
1               5

<210> SEQ ID NO 36
<211> LENGTH: 8
<212> TYPE: PRT
<213> ORGANISM: artificial sequence
<220> FEATURE:
<223> OTHER INFORMATION: L1-3B

<400> SEQUENCE: 36

Arg Tyr Pro Ala Gln Pro Gly Ser
1               5
```